United States Patent [19]
Iversen et al.

[11] Patent Number: 6,124,271
[45] Date of Patent: Sep. 26, 2000

[54] **METHOD AND CONJUGATE FOR TREATING *H. PYLORI* INFECTION**

[75] Inventors: Patrick L. Iversen, Corvallis, Oreg.; Randall Brand, Omaha, Nebr.; Dwight D. Weller; James E. Summerton, both of Corvallis, Oreg.

[73] Assignees: AVI BioPharma, Inc.; The Board of Regents of the University of Nebraska

[21] Appl. No.: 09/012,198

[22] Filed: Jan. 23, 1998

Related U.S. Application Data

[63] Continuation-in-part of application No. 08/848,844, Apr. 30, 1997, Pat. No. 6,030,941.
[60] Provisional application No. 60/036,366, Jan. 24, 1997.
[51] Int. Cl.[7] ............................ A61K 31/70; C07H 21/00
[52] U.S. Cl. ................................. 514/44; 536/24.5
[58] Field of Search .................................. 435/6, 29, 32, 435/252.1; 514/44; 536/24.5, 24.32

[56] References Cited

U.S. PATENT DOCUMENTS

| | | | |
|---|---|---|---|
| 5,409,903 | 4/1995 | Polak et al. | 514/23 |
| 5,420,019 | 5/1995 | Theofan et al. | 435/69.1 |
| 5,426,025 | 6/1995 | Reeves et al. | 435/6 |
| 5,434,253 | 7/1995 | Thompson et al. | 536/23.2 |
| 5,977,340 | 11/1999 | Pirotzky et al. | 536/24.5 |

FOREIGN PATENT DOCUMENTS

96/29399  9/1996  WIPO.

OTHER PUBLICATIONS

Stein. Keeping the biotechnology of antisense in context. Nature Biotechnology 17: 209, Mar. 1999.

Rahman, M.A., et al., "Antibacterial activity and inhibition of protein synthesis in *Escherichia coli* by antisense DNA analogs". Antisense Research and Development 1 (1991), 319–327.

*Primary Examiner*—Robert A. Schwartzman
*Assistant Examiner*—Thomas G Larson
*Attorney, Agent, or Firm*—Peter J. Dehlinger; Iota Pi Law Group

[57] ABSTRACT

A method and comjugate for treating *H. pylori* infection in a subject are disclosed. The conjugate is composed of (a) a nuclease-resistant antisense oligomer effective to inhibit *H. pylori* infection in the subject by base-specific Watson-Crick binding to an *H. pylori* mRNA transcript, and (b) a transport moiety conjugated to the oligomer. The transport moiety is effective to facilitate uptake of the conjugate from the environment of the stomach into the cytoplasm of *H. pylori* cells by active transport or by pH-gradient transport across of the cell membrane of *H. pylori*. The conjugate is administered by oral route, preferably in a swellable polymer bolus designed to release the conjugate in sustained release.

15 Claims, 9 Drawing Sheets

METHOD AND CONJUGATE FOR TREATING *H. PYLORI* INFECTION

This application claims the priority of U.S. provisional patent application for "Novel Compositions and Methods for Oral Treatment of Gastrointestinal Disorders", Ser. No. 60/036,366, filed Jan. 24, 1997, and is a continuation in part of U.S. patent application for "Polymer Composition for Delivering Substances in Living Organisms", Ser. No. 08/848,844, filed Apr. 30, 1997 now U.S. Pat. No. 6,030,941. Both applications are incorporated herein by reference.

FIELD OF THE INVENTION

The present invention relates to a method and antisense conjugate for inhibiting *H. pylori* infection, and to a composition for oral delivery of the conjugate.

BACKGROUND

*Helicobacter pylori* is a naturally competent gram negative bacteria with spiral- or S-shaped morphology which infects the lining of the stomach. *H. pylori* was originally cultured from gastric biopsy in 1982 and was placed in the Campylobacter genus based upon gross morphology. In 1989, the new genera of Helicobacteracea was proposed and accepted, with *H. pylori* being its sole human-infectious member (Blaser, M., Scientific American, (1996) p. 104.)

Strong evidence supports a causal role for *H. pylori* in chronic superficial gastritis, peptic ulcer disease, and chronic atrophic gastritis leading to gastric adenocarcinoma. Human subjects who ingested *H. pylori* developed gastritis, a condition that was resolved after the infection was eliminated by antibiotic treatment.

*H. pylori* infection is found in virtually all cases of chronic superficial gastritis and non-steroidal anti-inflammatory drug (NSAID)-associated peptic ulcer disease, and *H. pylori* infection may increase the risk of gastric cancer (Parsonnet, J., et al., N. Engl. J. Med. 325:1127–1131 (1991). In developed countries, about half of the population has been colonized with *H. pylori* by age 50, and in developing countries, colonization is common even among children. Further, one out of ten infected individuals will develop peptic ulcer disease in the course of a lifetime.

Current clinical recommendations from the NIH Consensus Conference is to eradicate *H. pylori* in any infected patients with gastric ulcer disease. This is significant in that 4–5 million Americans get peptic ulcer disease and spend billions of dollars each year in health care costs for treatment.

Current therapy is directed at eradication of *H. pylori* infection consists of antibiotics, often in conjunction with bismuth subsalicylate or proton pump inhibitors. Best success rates have been achieved with therapies which include two or more antibiotics administered for two weeks or more. Dual therapies which have been proposed include, for example, clarithromycin and omeprazole (Wurzer, H., et al, (1997), Aliment Pharmacol Ther. 11(5):943–952.) Triple therapies that have been reported are omeprazole plus clarithromycin and either tinidazole or tetracycline (Zullo. A., et al., Am J Gastroenterol, (1997) 92(11):2029–2031) and amoxycillin with clarithromycin and omeprazole (Wurzer, supra). Quadruple therapies involving three antibiotics and bismuth are also known (Graham. D. Y., et al, (1997) Alimen Pharmacol Ther 11(5):935–938).

Important complications of antibiotic treatment include direct side effects from the medications such as diarrhea, nausea, and rash. More importantly, from a public health care standpoint, is the development of resistant strains of *H. pylori* for a particular antibiotic. A novel approach for inhibiting *H. pylori* infection would therefore be highly desirable. To minimize complications, this approach should be local (i.e. not well absorbed), easy to administer, without significant side effects, and refractory to the development of bacterial resistance.

SUMMARY OF THE INVENTION

The invention includes, in one aspect, an antisense conjugate for use in treating *H. pylori* infection. The conjugate is composed of (a) a nuclease-resistant antisense oligomer effective to inhibit *H. pylori* infection in the subject by base-specific Watson-Crick binding to an *H. pylori* mRNA transcript, and (b) a transport moiety conjugated to the oligomer. The transport moiety is effective to facilitate uptake of the conjugate from the environment of the stomach into the cytoplasm of *H. pylori* cells by active transport or by pH-gradient transport across of the cell membrane of *H. pylori*.

Exemplary antisense oligomers have sequences that span the AUG start codon of an *H. pylori* vacA, cagA, cai, a porin, nixA, pfr, neutrophil activating factor, urease, metal-binding polypeptide, or copper-binding protein gene. Representative oligomer base sequences are identified by SEQ ID NOS: 1–11, preferred sequences being identified by SEQ ID NOS: 1, 5 and 6. A preferred antisense oligomer has an uncharged morpholino backbone.

In one general embodiment, the transport moiety is a sugar, and uptake of the conjugate is by active transport. Preferred sugars are those, such as D-galactose or L-arabinose, that are not absorbed from the gut.

In another general embodiment, the transport moiety is a polypeptide containing one or more pairs of carboxyl groups, where (i) the carboxyl groups of a pair are separated by zero, two or three amino acids, (ii) the polypeptide has a length of between about 8 and about 100 amino acid residues, and (iii) the polypeptide is effective to undergo a reversible transition between a lipophilic form at the pH of the stomach, and a hydrophilic form at the pH of the cytoplasm of *H. pylori* cells, and uptake of the conjugate is by pH-gradient transport. The polypeptide preferably includes an initiator at one end region of the polypeptide, to facilitate entry of the end region into the membrane of *H. pylori* cells.

In another aspect, the invention includes a method of treating *H. pylori* infection in a subject, by orally administering the above conjugate in a therapeutically effective amount. In practicing the method, the conjugate is preferably contained within a swellable polymer matrix designed for sustained conjugate release in the stomach.

These and other objects and features of the invention will become more fully apparent when the following detailed description is read in conjunction with the accompanying figures and examples.

DETAILED DESCRIPTION OF THE INVENTION

I. Definitions

Figure 1A:
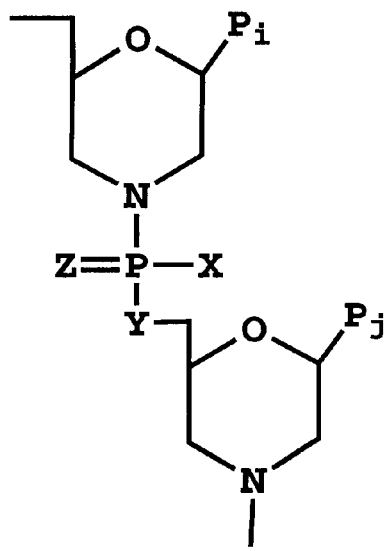
FIGS. 1A–1D illustrate exemplary uncharged morpholino backbone structures suitable for the conjugate of the invention.

The terms below, as used herein, have the following meanings, unless indicated otherwise:

An "antisense oligomer" refers to an oligomer having a sequence of nucleotide bases and a subunit-to-subunit backbone that allows the oligomer to hybridize to a target sequence in an mRNA by Watson-Crick base pairing, to form an RNA/oligomer duplex in the target sequence. The oligomer may have exact sequence complementarity to the target sequence or near complementarity, as long as the hybridized duplex structure formed has sufficient stability to block or inhibit translation of the mRNA containing the target sequence, or inhibit gene transcription, where the antisense oligomer is a double-stranded binding agent.

A "nuclease resistant" antisense oligomer is one whose backbone is not susceptible to nuclease cleavage of a phosphodiester bond. The backbone of the oligomer may be charged or uncharged.

A "transport moiety" acts through an active transport mechanism if the moiety is transported across the *H. pylori* cell membrane, in an outside-to-inside direction, by an energy-dependent active transport mechanism. A "transport moiety" acts through a pH-gradient transport mechanism if the moiety is transported across the *H. pylori* cell membrane, in an outside-to-inside direction, by the lower-outside/higher-inside pH gradient across the *H. pylori* cell membrane in the environment of the stomach.

An "*H. pylori* gene" as used herein, refers to polynucleotide sequences encoded by *H. pylori*, including variants thereof, and encoding a specified *H. pylori* protein.

"Treating *H. pylori* infection" means preventing *H. pylori* infection, eradicating or reducing the number of *H. pylori* bacteria at the site of infection, or reducing the pathogenicity of *H. pylori*, e.g., by blocking toxicity or inflammation due to the presence of *H. pylori* infection in the subject, or the ability of *H. pylori* to colonize the gut.

"Therapeutically effective amount" refers to an amount administered to a mammalian host, either as a single dose or as part of a series, that is effective in treating *H. pylori* infection, i.e., of achieving one of the above treatment effects.

II. Oligomer Conjugate

This section describes the selection of suitable *H. pylori* antisense sequences, suitable antisense oligomers and transport moieties, and synthesis of the oligomer/transport moiety conjugate of the invention.

A. Oligomer sequences

The antisense oligomer is targeted against expression of an *H. pylori* gene which contributes to the pathogenicity or viability of the bacteria in the environment of the stomach. In general three types of target genes are contemplated: (1) genes that encode a toxin, (2) genes that promote an inflammatory response to the infection, and (3) genes necessary for growth, viability, and/or colonization of *H. pylori* cells in the stomach. Preferred target genes, and the rationale for their selection are as follows:

(1) Genes which encode a toxin vacA: The vacA gene encodes a unique protein toxin which induces cytoplasmic vacuolation in eukaryotic cells and eventual cell death. A strong correlation exists between presence of specific vacA genotypes, cytotoxin activity, and peptic ulceration. VacA cytotoxin appears to play an important role in inducing gastric epithelial necrosis (Cover, TL (1996) Mol Microbiol 20(2):241–246). Blocking expression of the vacA gene would reduce gastric epithelial damage associated with *H. pylori* infection.

cagA/cai: The cagA (cytotoxin-associated gene A) gene (also known as cytotoxicity associated immunodominant antigen, cai) encodes an immunodominant cell-surface protein, the expression of which appears to be closely associated with expression of the VacA toxin (Covacci A et al. (1993) Proc Natl Acad Sci USA 90(12):5791–5795). Blocking expression of the cagA gene may reduce inflammation and gastric epithelial damage associated with *H. pylori* infection.

(2) Genes which promote an inflammatory response to *H. pylori* infection napA: neutrophil-activating factor is a 150 kDal protein which is a polymer of identical 15K subunits. NapA promotes activation of human neutrophils, characterized by increased expression of neutrophil CD11b/CD18 and increased adhesiveness to endothelial cells (Evans D. J. Jr, et al (1995) Infect Immun 63(6):2213–2220). Blocking expression of the napA gene would reduce the inflammatory response associated with *H. pylori* infection.

(3) Genes necessary for growth, viability, and/or colonization urease: Urease, the most abundantly expressed protein in *H. pylori*, is a nickel-dependent enzyme which catalyzes the hydrolysis of urea to yield ammonia and carbonic acid. Urease aids in colonization of the host by neutralizing gastric acid and providing ammonia for bacterial protein synthesis. Host tissues can be damaged directly by the urease-mediated generation of ammonia and indirectly by urease-induced stimulation of the inflammatory response, including recruitment of leukocytes and triggering of the oxidative burst in neutrophils. Blocking expression of the urease gene would inhibit *H. pylori* colonization in the host, reduce bacterial protein synthesis, and reduce the inflammatory response associated with *H. pylori* infection.

nixA: Accessory proteins are required for nickel ion insertion into the urease apoenzyme. One such protein is NixA, a high-affinity nickel transport protein. Blocking expression of the nixA gene, alone or together with an abc gene (below), would reduce the activity of *H. pylori* urease, and produce the effects described above.

abcABCD: The abc gene cluster, which consists of four open reading frames, is also involved in the production of catalytically active urease. One protein product of this cluster is homologous to a component of an *E. coli* ATP-dependent nickel transport system. By insertional inactivation and allelic exchange in *H. pylori*, it was shown that mutation of the abcD gene resulted in an 88% decrease in urease activity, and a double mutant of nixA and abcC resulted in the near abolishment of urease activity, without affecting urease apoenzyme synthesis (Hendricks J. K., et al., (1997) J Bacteriol 179(18):5892–5902; Mobley, H. L., et al., (1995) Mol. Microbiol. 16:97–109). Blocking the expression of one or more genes in the abc cluster, alone or together with the nixA gene, would reduce the activity of H. pylori urease, and produce the effects described above.

copA, copP: The copA and copP genes encode a putative copper-transporting P-type ATPase and a putative copper binding protein, respectively. Disruption of the copA gene causes cupric ion accumulation within the cells. CopA and CopP are proposed to comprise a cation-transporting system which is associated with copper export out of H. pylori (Ge Z., et al., (1996) FEMS Microbiol Lett 145(2): 181–188). Blocking expression of the copA or copP genes would render H. pylori hypersensitive to cupric ion in the gut and/or inhibit Cu-dependent enzymes.

pfr: Pfr is an abundant 19.3 kDal protein homologous to a nonheme ferritin protein found in E. coli. Pfr forms paracrystalline inclusions in the H. pylori cytosol and binds iron in a heme-independent manner (Frazier B. A., et al. (1993) J Bacteriol 175(4):966–972). Blocking expression of the pfr gene would render H. pylori hypersensitive to iron and/or inhibit Fe-dependent enzymes.

hpn: The hpn gene encodes 7 kDal protein which consisting of 60 amino acids, 28 of which are histidine. Hpn protein strongly binds Ni and Zn (Gilbert J. V. et al (1995) Infect. Immun. 63(7):2682–2688). Blocking expression of the hpn gene would render H. pylori hypertensive to Ni and/or Zn, and inhibit Ni or Zn-dependent enzymes such as urease.

The antisense oligomer may be 100% complementary to the target sequence, or may include mismatches, e.g., to accommodate bacterial variants, as long as the hybrid duplex formed between the oligomer and target sequence is sufficiently stable in the cell to block or inhibit translation of the target mRNA. The number of mismatches allowed will depend on the type and length of the oligomer, the percentage of G:C basepair in the duplex and the position of the mismatch(es) in the duplex, according to known principles of duplex stability.

The appropriate length of the antisense oligomer to allow stable, effective binding combined with good specificity is about 10 to 40 nucleotide base units, and preferably about 15 to 25 base units. Mismatches, if present, are less destabilizing toward the end regions of the hybrid duplex than in the middle. Oligomer bases that allow degenerate base pairing with target bases are also contemplated, assuming base-pair specificity with the target is maintained.

The effectiveness of a given antisense oligomer molecule in inhibiting the target H. pylori gene may be determined by screening methods known in the art. For example, a conjugate of the oligomer and transport moiety is incubated with an H. pylori cell culture, and the presence or absence of the encoded protein is determined by standard techniques such as ELISA or Western blotting.

Candidate compounds are also evaluated, according to well known methods, for acute and chronic cellular toxicity, such as the effect on protein and DNA synthesis as measured via incorporation of $^3$H-leucine and $^3$H-thymidine, respectively.

It is generally desirable that non-specific binding of the oligomeric molecule to non-target sequences is limited. Although some non-sequence-specific interactions of such oligomers may show therapeutic effects, such interactions often produce unwanted side effects. To test for non-specific binding effects, control sequences such as sense or nonsense sequences, or sequences containing mismatched bases, may be included in screening tests. Excess targeted protein or mRNA may also be added to the cell culture to see if the effect of the antisense oligomer is reversed (Bennett).

Exemplary oligomers having the base sequences shown in Table I are designed for mRNA-specific inhibition of expression of the genes indicated. The locations of the target bases, as numbered in the GenBank sequence database, are indicated at the right in the table. The orientation of the antisense sequences is shown in a 5' to 3' direction, by convention. In a hybrid duplex in which the target coding sequence is shown a 5' to 3' direction (by convention), the order of the antisense oligomer sequences would be reversed; that is in a 3' to 5' direction.

Each sequence in the table was selected to (i) span the ATG start codon of the indicated gene, with the CAT complement of the start codon (expressed in a 5' to 3' direction) being positioned near the center of the oligomer, (ii) have a total length of about 20–24 bases, and (iii) terminate, at the 5' end, at a G base, which may confer stability on the duplex. The table also identifies the sequence ID number of each sequence.

Preferred antisense sequences are those identified by SEQ ID NOS: 1, 5, and 6, for inhibiting expression of the urease, vacA, and napA genes, respectively.

TABLE 1

| Gene | GenBank Accession and NID | SEQ ID NO: | Antisense sequence (5' –> 3') | Position |
|---|---|---|---|---|
| Urease | A31515 g1567115 | 1 | GGGTGAGTTTCATCTCATTCTCC | 54–76 |
| His-rich Metal Binding Polypeptide (hpn) | U26361 g836666 | 2 | GGTGTGCCATGATGACTCCTTTG | 438–460 |
| ATPase (copA) | L33259 g1518875 | 3 | GATTCTTTCATGCGCTTTTA | 191–210 |
| Copper Binding Protein (copP) | L33259 g1518875 | 4 | GTAACTTTCATTCAATGATC | 2429–2448 |
| Vacuolating Cytotoxin (vacA) | U29401 g984359 | 5 | GTTGTATTTCCATTTTCTTCCT | 337–358 |

TABLE 1-continued

| Gene | GenBank Accession and NID | SEQ ID NO: | Antisense sequence (5' → 3') | Position |
| --- | --- | --- | --- | --- |
| Cytotox. Assoc. Immunodominant Antigen (cai/cagA) | X70039 g394912 | 6 | GTTAGTCATTGTTTTCTCCTT | 524–543 |
| Nickel-Transport (nixA) | Z48742 g732733 | 7 | GTTATTGGCCATAAAGAGCAA | 1499–1519 |
| Nonheme Iron-Containing Ferritin (pfr) | S54729 g265360 | 8 | GTCTTTTGATAACATAGTATCT | 290–311 |
| Neutrophil Activating Protein (napA) | U16121 g560031 | 9 | GTTTTCATCAAAAGTCCTTTTT | 50–71 |
| Putative Transporter Component abcC | AF010307 g2440005 | 10 | GTTTTTTAATTCTACTACCATCGT | 940–963 |
| Putative Transporter Component abcD | AF010307 g2440005 | 11 | GCATTTGAGAAATCATTTTAATC | 1921–1943 |

B. Antisense oligomers

The antisense oligomers of the invention are nuclease-resistant oligomers having, in addition to a base sequence complementary to a selected target sequence, an oligomer backbone, defined by the oligomer subunits and linkages, that allow for oligomer to bind to the target sequences by Watson-Crick base pairing between complementary bases in the target and oligomer.

A number of nuclease-resistant oligomers having this property are known (see, for example, Uhlmann et al., *Chemical Reviews*, 90: 543–584 (1990). Exemplary oligomers with charged backbones include phosphorothioates, 3'-NHP(O)(O—)O-5'phosphoramidates (WO 95/25814), and oligo-2' fluoronucleotide N3'→P5' phosphoramidates (U.S. Pat. No. 5,684,143).

Non-ionic oligonucleotide analogs, i.e., oligomers with uncharged backbones, include phosphotriester- and methylphosphonate-linked DNA (Miller et al., *Biochemistry* 18:5134 (1979); Miller et al., *J. Biol. Chem.* 255:6959 (1980), carbamate-linked nucleosides (Stirchak, E. P. et al., *J. Org. Chem.* 52:4202 (1987), phosphoroamidate-linked DNA (Froehler et al., *Nucleic Acids Res.* 16:4831 (1988), and peptide nucleic acids (PNAs) (WO 92/20703).

One preferred nonionic antisense oligomer is an uncharged-backbone morpholino oligomer of the type described, for example, in U.S. Pat. No. 5,166,315, which is hereby incorporated by reference. These oligomers afford high target binding affinity, especially for RNA targets. They are also resistant to degradation by nucleases.

Morpholino oligomers are composed of morpholino subunit structures preferably linked together by uncharged, phosphorous-containing linkages, one to three atoms long, joining the morpholino nitrogen of one subunit to the 5' exocyclic carbon of an adjacent subunit. Linked to each subunit is a purine or pyrimidine base-pairing moiety effective to bind, by base-specific hydrogen bonding, to a base in a target polynucleotide.

Figure 1B:
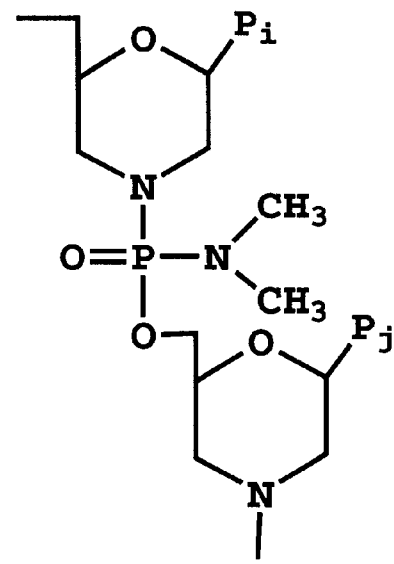
Figure 1C:
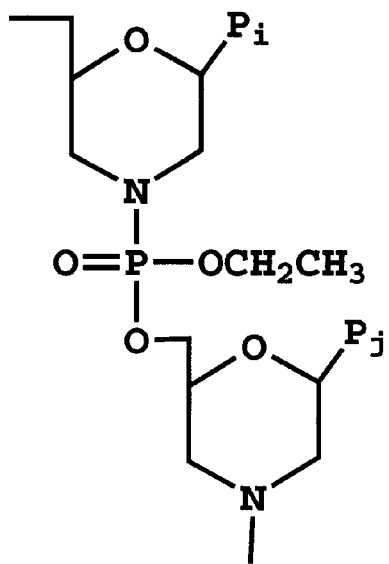
Figure 1D:
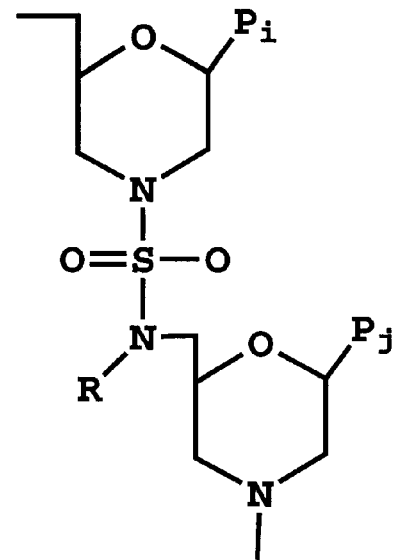
Figure 1E:
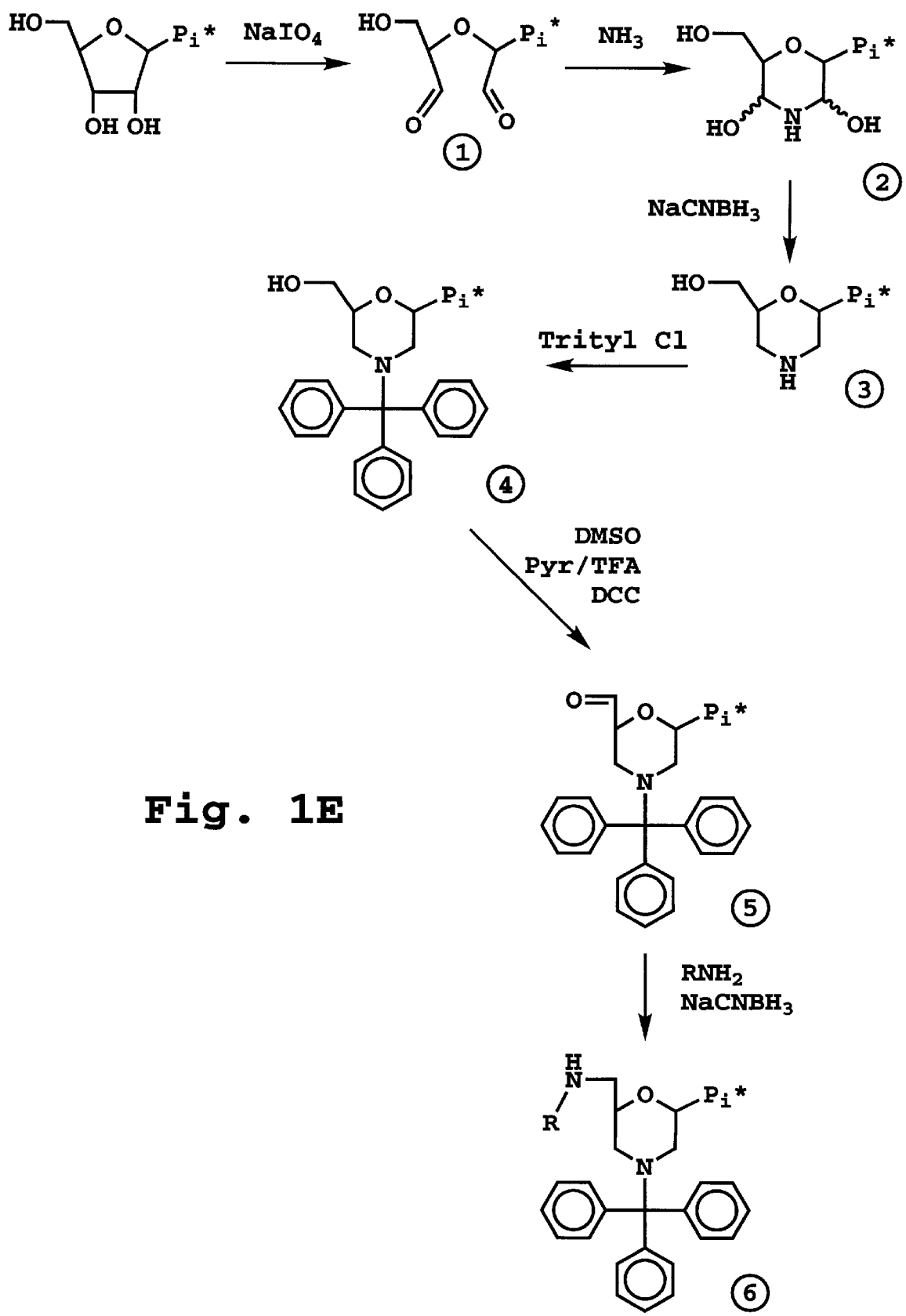
FIG. 1E illustrates the synthesis of 5'-OH morpholino subunits.

FIG. 1E illustrates steps in the synthesis of 5'-OH morpholino subunits, as detailed in Example 1. The subunit is converted to the 5' amine by the method detailed in Example 2. Preparation of such subunits is also described in detail in U.S. Pat. No. 5,185,444 (Summerton and Weller, 1993), which is hereby incorporated by reference.

FIGS. 1A–1D illustrate preferred backbone structures, showing two morpholino subunits of a multisubunit oligomer. Each ring structure includes a purine or pyrimidine or related hydrogen-bonding moiety, represented by $P_i$ and $P_j$, attached to the backbone morpholino moiety through a linkage in the β orientation. The purine or pyrimidine base-pairing moieties in the oligomer are typically adenine, cytosine, guanine, uracil or thymine.

In the structure of FIG. 1A, the atom Y linking the 5' morpholino carbon to the phosphorous group may be sulfur, nitrogen, carbon, or oxygen; nitrogen and oxygen are preferred, and oxygen is particularly preferred. Z represents sulfur or oxygen, and is preferably oxygen.

The X moiety pendant from the phosphorous may be any of the following: fluorine, alkyl or substituted alkyl, alkoxy or substituted alkoxy, thioalkoxy or substituted thioalkoxy, or unsubstituted, monosubstituted, or disubstituted nitrogen, including cyclic structures. Several cyclic disubstituted nitrogen moieties which are suitable for the X moiety are morpholine, pyrrole, and pyrazole. Preferred embodiments of X are alkoxy and dialkyl-substituted nitrogen. FIGS. 1B and 1C show preferred embodiments of the general structure represented by FIG. 1A. FIG. 1D shows an additional preferred structure, having a sulfonamide linkage between morpholino subunits.

The structures shown are representative of several non-ionic linkages in morpholino backbone structures suitable for use in the invention. Reference is made to above cited U.S. Pat. No. 5,185,444 for details on oligomer synthesis. A preferred repeating subunit linkage is the phosphoramidate linkage illustrated in FIG. 1B.

Binding of a morpholino oligomer to a target has been shown to give strong inactivation, due to the greater binding affinity noted above, and because the oligomer/target duplex is not susceptible to duplex unwinding mechanisms in the cell. Further, in therapeutic applications involving cellular uptake of the compound, the uncharged morpholino polymer is more efficiently transported into *H. pylori* cells by the transport moiety in the conjugate of the invention than are oligomers with charged backbones.

Although targeting of a messenger RNA sequence is preferred, a double-stranded DNA, i.e., bacterial gene, may be targeted by using a non-ionic probe designed for sequence-specific binding to major-groove sites in duplex DNA. Oligomers suitable for forming base-specific triplex structures with a target duplex DNA are described, for example, in U.S. Pat. No. 5,405,938.

C. Transport moiety

The conjugate of the invention also includes a transport moiety covalently attached to the antisense oligomer, for facilitating uptake of the oligomer from the environment of the stomach into cytoplasm of *H. pylori* bacterial cells colonizing the gut.

The transport moiety acts to facilitate uptake of the conjugate either by an active transport, i.e., energy-dependent membrane-receptor mechanism, or by a pH-gradient mechanism that relies on the lower-outside/higher inside pH gradient of *H. pylori* cells in the environment of the stomach, as discussed below.

Preferred active transport moieties include monosaccharide sugars, such as glucose, mannose, D-galactose and L-arabinose. The latter two sugars are not absorbed from the gut, and therefore have the advantage of limited uptake into the bloodstream of the patient. Methods for coupling a sugar moiety to a morpholino oligomer are detailed below.

Sugar, e.g., glucose transport is saturable, energy dependent and temperature dependent. The *H. pylori* glucose transporter is unique in that it is not inhibited by cytochalasin B, phloretin or phloridzin but is inhibited by arniloride (Mendz et al., (1995) Biochem. Biophys. Acta 1244:269). Structure activity studies indicate that are high affinity transport molecules. Two transporters have been identified as hpCopA and hpCopP for glucose transport. The hpCopA transporter is a P-type ATP-ase with 29–38% homology with other bacterial ATPases. The hpCopP transporter is similar to MarP periplasmic mercury ion transporters.

Certain antibiotics, including nitroheterocyclic drugs, such as metronidazole, and tetracyclines are actively internalized into bacteria, and represent other types of active-transport moieties that are suitable.

A pH-gradient polypeptide transport moiety is a polypeptide that is designed to undergo a reversible transition between an α-helical, hydrophobic form at the low pH of the stomach, and a charged hydrophilic form at the higher pH within the cytoplasm of an *H. pylori* cell.

Figure 2:
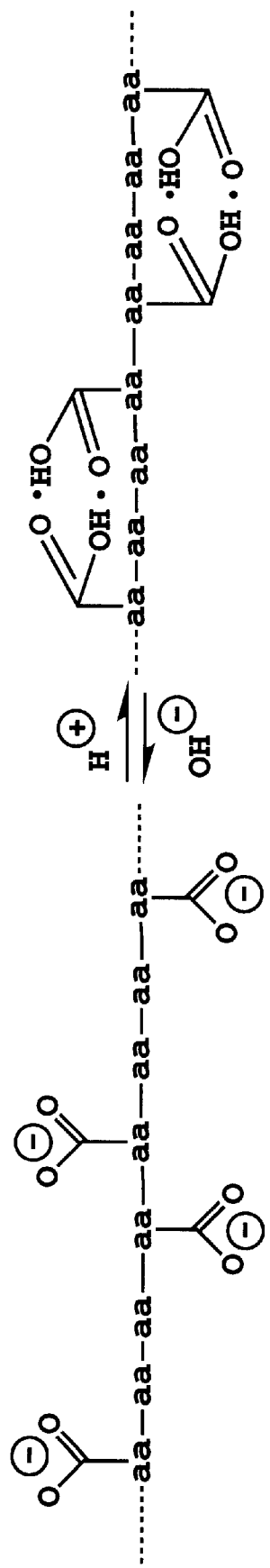
FIG. 2 illustrates the transition of a polypeptide transport moiety between a low-pH, α-helical hydrophobic form, and a high-pH, hydrophilic form.

The moiety has one or more pairs of side-chain carboxyl groups, such as glutamate and aspartate groups, separated by zero, three, or four amino acids along the polypeptide chain, and a polypeptide chain length of between 8 and up to 200 amino acids, preferably between 10–50 residues. As illustrated in FIG. 2, pairs of side-chain carboxyl groups, when protonated at low pH, form intrachain hydrogen bonds that convert the polypeptide from a charged, lipophilic form (at left in the figure) to an α-helical, lipophilic form (at right in the figure).

Construction of transport moiety polypeptides suitable for the present invention are detailed in PCT application PCT/US97/07335, International Publication No. WO97/40854 for "Polypeptide Conjugates for Transporting Substances Across Cell Membranes", published Nov. 6, 1997, which is incorporated herein by reference. Briefly, studies with CPK molecular models were used to predict the preferred spacing of acid side chains to provide the desired hydrogen-bonded structures. Subsequent octanol/water and pentanol/water partitioning studies with suitable polypeptide sequences verified that good lipid solubility can indeed be achieved at low pH if acid pairs, selected from aspartic and glutamic, are suitably spaced.

Table 2 lists these spacings which provide the desired shielding of polar sites of acid pairs at low pH.

TABLE 2

E-E
D-E
E-X-X-E
E-X-X-D
E-X-X-X-E
E-X-X-X-D
D-X-X-X-E where: E = glutarnic acid
D = aspartic acid
X = amino acid As can be seen from the table, spacings of zero, two, or three amino acids between carboxyl side chain amino acids are effective. Of these, spacings of two or three amino acids between carboxyl side chain amino acids are preferred.

In order to form an α-helix with suitably spaced pairs of carboxyl side chains, the polypeptides of the invention should be at least 8 amino acids in length, and preferably at least 10–15 amino acids in length.

As discussed further below, entry into a cell membrane appears to be initiated at a terminus of the polypeptide. Three general strategies have been devised to enhance entry of the polypeptide terminus into the cell membrane, to initiate transmembrane transport of the polypeptide and uptake of the antisense oligomer. All of the strategies are aimed at making the "entry" terminal of the polypeptide, i.e., the free end (which is typically the end opposite the oligomer-conjugation end) more hydrophobic, by placing an initiator structure at the entry end.

The first strategy is to include an initiator polypeptide sequence, which may be an end-region extension of a polypeptide. The extension contains fewer than about 50% acidic residues, or, in the case of a homopolymer of acidic amino acids, a more hydrophobic, alpha-helix forming region containing fewer than about 50% acidic, e.g., glutamate residues.

The second and third strategies involve shielding or removing polar sites. A polypeptide in an α-helical conformation typically contains multiple polar sites at both the C-terminus and the N-terminus which are not shielded by intramolecular hydrogen bonding. These unshielded polar and ionic sites constitute a substantial bar to initiation of polypeptides into lipid layers, due to the presence of solvated counterions and water of solvation, and the propensity of the polar termini to assume a non-α-helical conformation. Deleting the terminal charge and shielding or removing one or more of these polar sites can improve lipid solubility, particularly in the case of short or highly polar polypeptides.

Figure 3A:
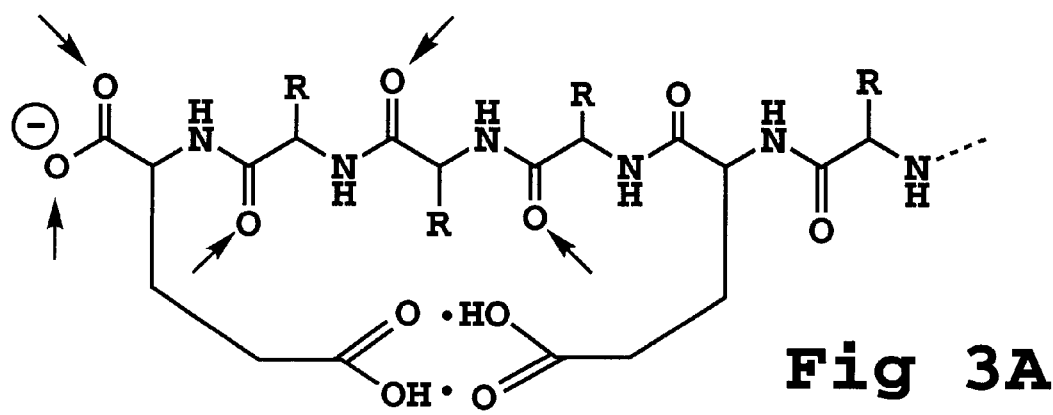
FIGS. 3A–3C illustrate various C-terminal end-capping strategies for a polypeptide transport moiety in the conjugate of the invention.
Figure 3B:
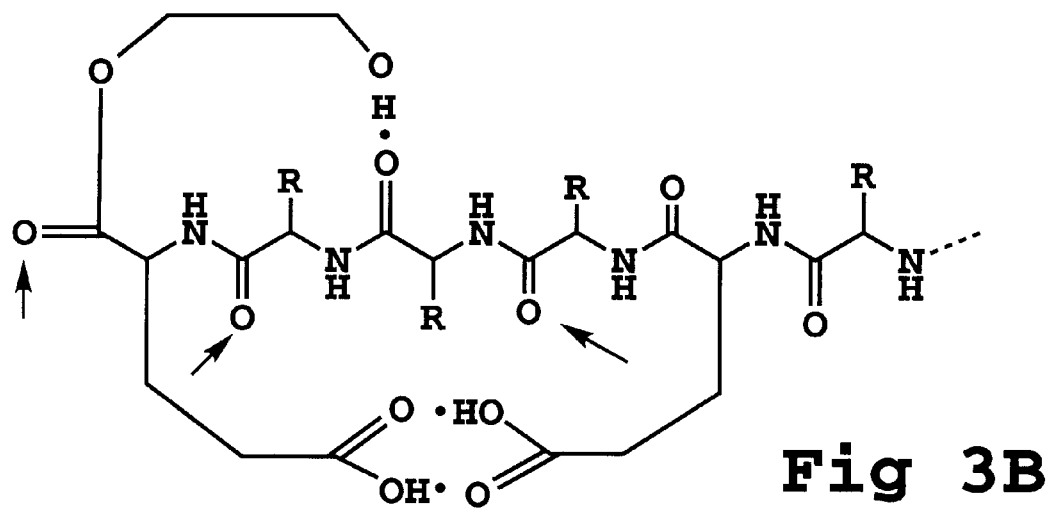
Figure 3C:
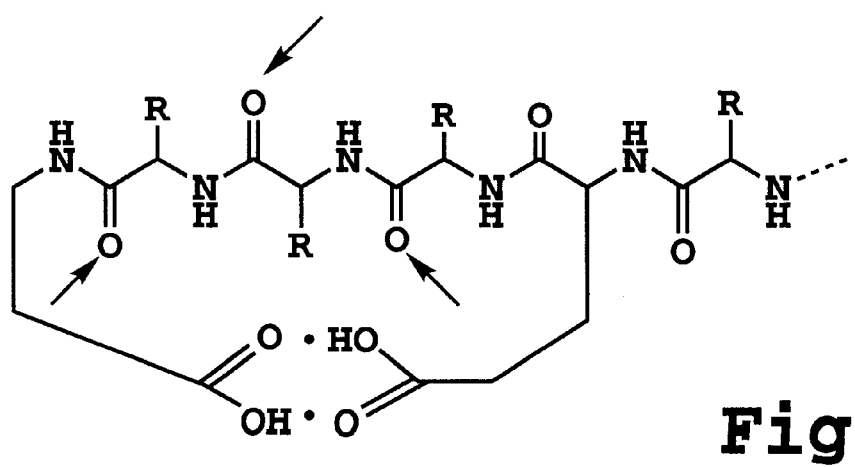

C-terminus shielding is illustrated in FIGS. 3A–3C. The C-terminus of a polypeptide typically contains three carbonyl groups and a negatively-charged carboxylate ion which are not shielded by intramolecular hydrogen bonding, as illustrated in FIG. 3A. One method for reducing the number of these unshielded terminal polar sites is to incorporate an α-ester, preferably a 2-hydroxyethyl ester, at the C-terminus, as illustrated in FIG. 3B. Polar sites may also be conveniently eliminated from the C-terminus by initiating the synthesis of the polypeptide on a support resin with β-alanine; the resulting structure is shown in FIG. 3C.

Figure 4A:
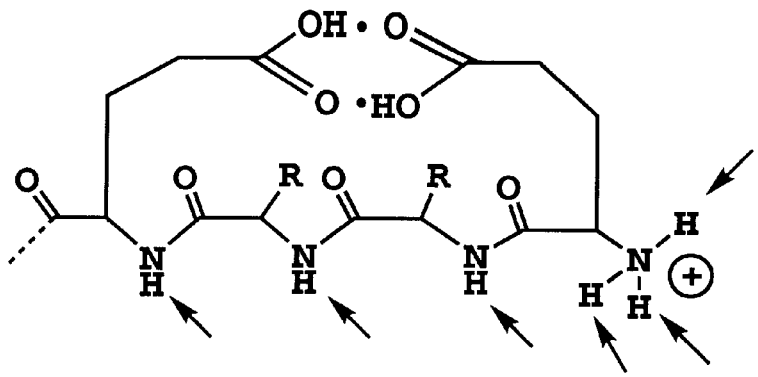
FIGS. 4A–4C illustrate various N-terminal end-capping strategies for a polypeptide transport moiety in the conjugate of the invention.
Figure 4B:
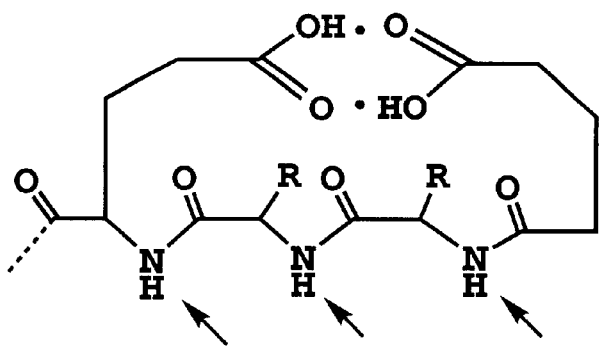
Figure 4C:
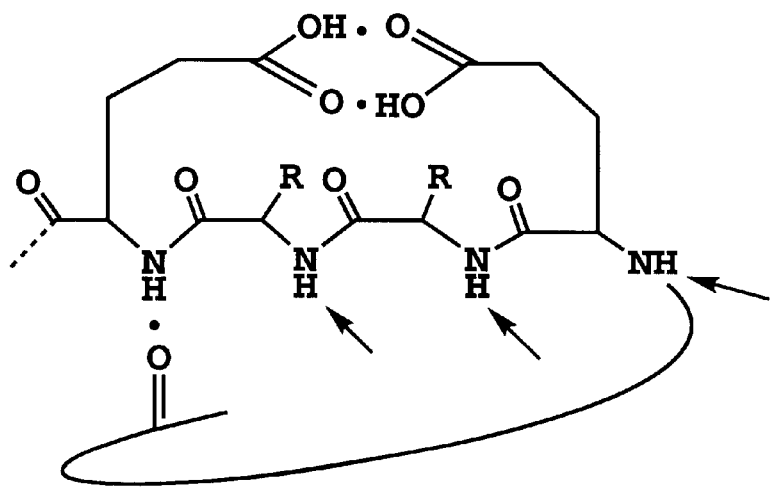
Figure 5:
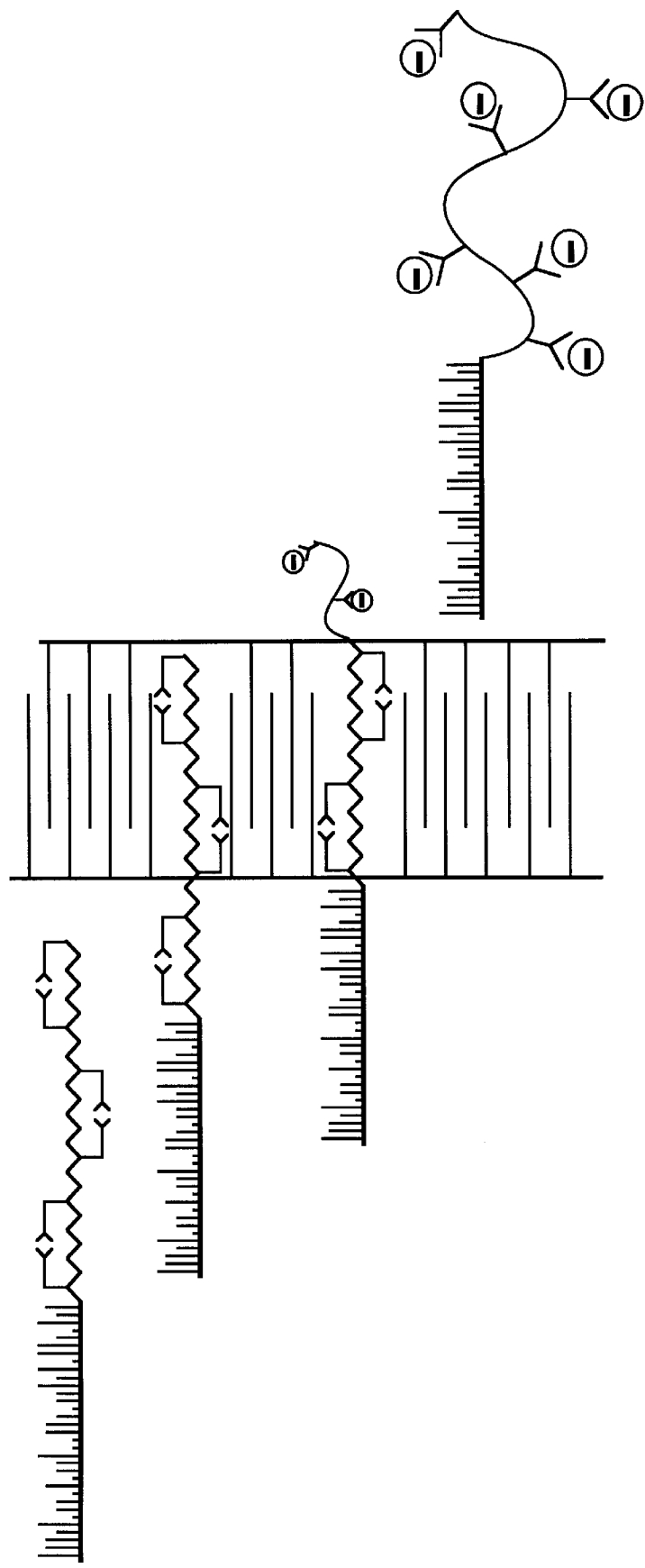
FIG. 5 illustrates the pH-gradient transport of an oligomer conjugate from the environment of the stomach into the cytoplasm of *H. pylori* cells, in accordance with one embodiment of the invention.

N-terminus shielding, most useful where the entry end of the polypeptide is its N terminus is illustrated in FIGS. 4A–4C. The N-terminus of a polypeptide typically contains three amide protons and a positively-charged protonated amine which are not shielded by intramolecular hydrogen bonding, as illustrated in FIG. 4A. Polar sites may be conveniently removed from the N-terminus by terminating the polypeptide with a diacid, as illustrated in FIG. 4B. Alternatively, polar sites can be shielded simply by acetylating the terminal amine, as illustrated in FIG. 4C. Hydrogen bonding occurs as shown when the polypeptide is in an α-helix. More extensive shielding of the N-terminus may be achieved by a novel structure, referred to as an N-crown, designed to shield all of the normally-exposed polar sites at the N-terminus of α-helices, as detailed in the above-cited PCT application.

Additional motive force for unidirectional transport is provided by ionization and hydration of the side-chain carboxyls once the polypeptide spans the membrane and encounters the higher-pH cellular cytosol. Thus a polypeptide having a high percentage of side chain carboxyls is expected to provide a high driving force to transport an attached compound across the membrane. Accordingly, a preferred class of polypeptides for use in the present invention includes those having 30%–100%, and preferably 50%–100%, glutamic acid content, and having an initiator structure as described herein at one terminus.

D. Conjugate synthesis

The transport moiety may be conjugated to the antisense oligomer by known conjugation methods, typically involving attachment to a 5'-hydroxyl or amino group of the oligomer, e.g. a morpholino oligomer, although attachment to a 3'-end group, e.g., the 3'-OH group of a ribose subunit, or the ring nitrogen or a morpholino subunit, is also contemplated.

Figure 6:
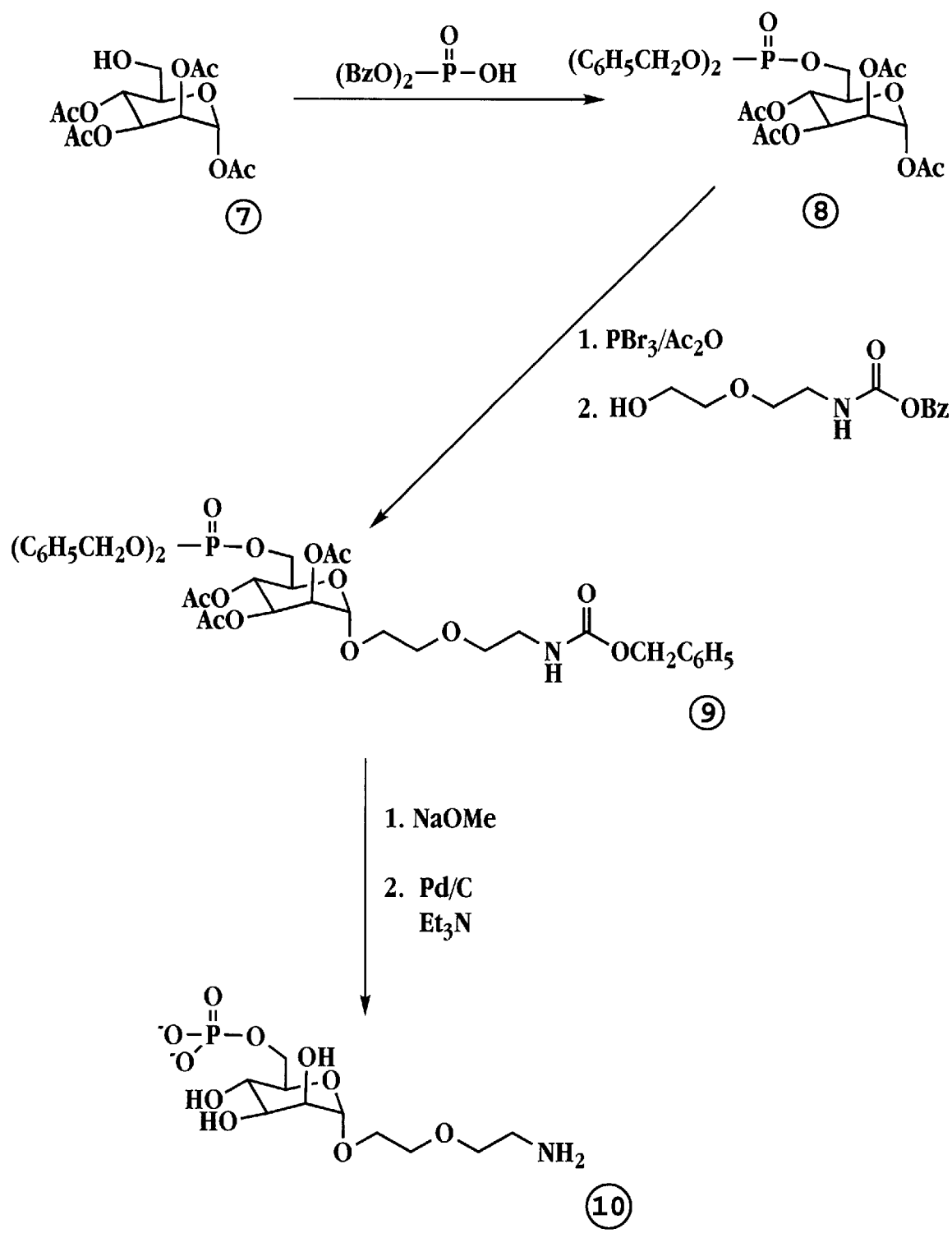
FIGS. 6 and 7 illustrate steps in the conjugation of a sugar transport moiety to a morpholino-backbone oligomer, to form an embodiment of the conjugate of the invention.
Figure 7:
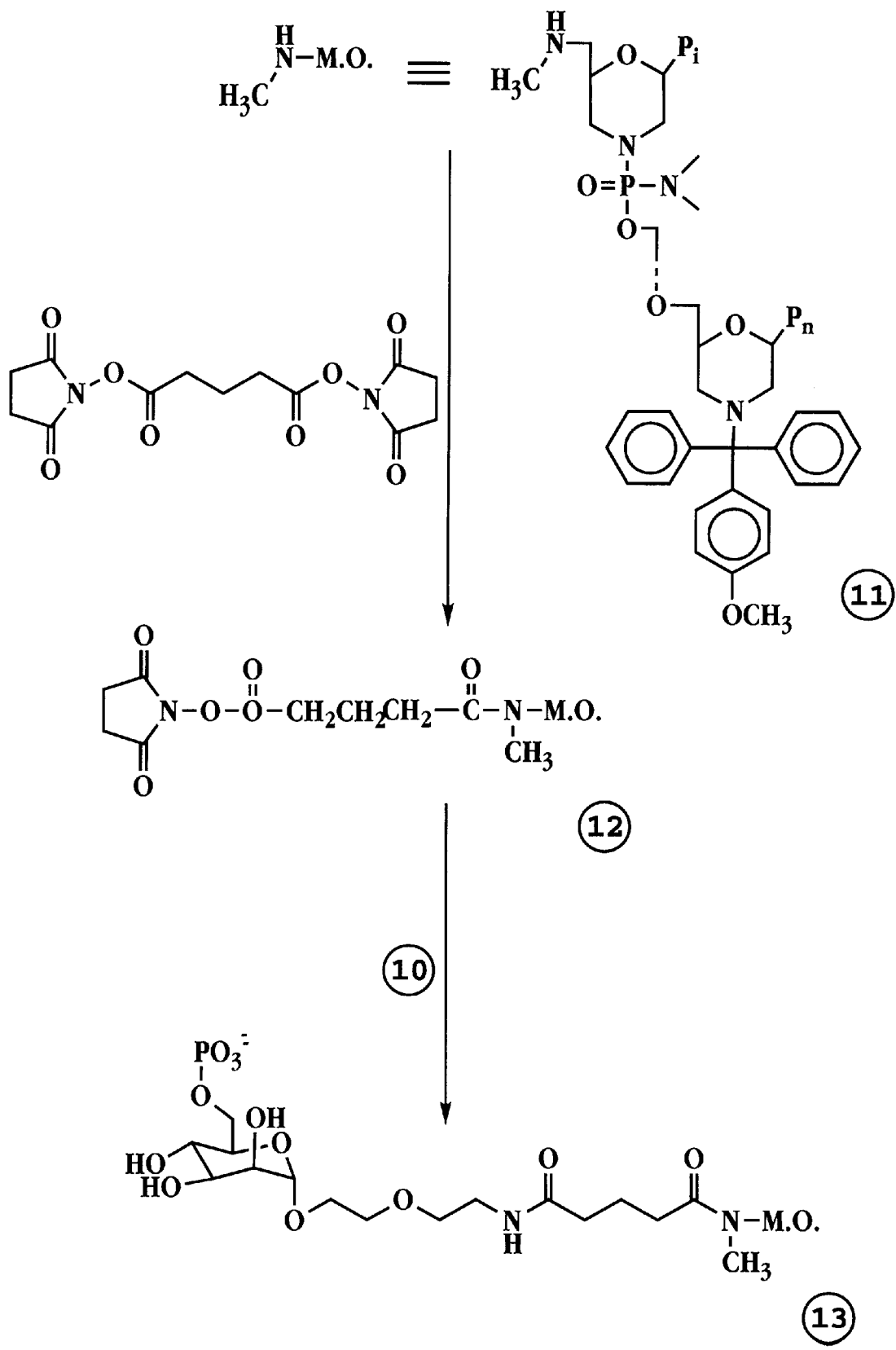

Coupling to a Saccharide. Attachment of a sugar to to an antisense oligomer is described in Examples 6–11, and illustrated in FIGS. 6 and 7, for the attachment of a 6-(dihydrogen phosphate)-α-D-mannopyranoside to the 5'-amino group of a morpholino oligomer. As shown in the Figures, α-D-mannopyranose-1,2,3,4-tetraacetate is phosphorylated, and the 2-acetyl group is converted to the bromide and then reacted with a carbamate-terminated PEG-OH spacer group. The ester and carbamate groups are then cleaved by hydrolysis, followed by hydrogenation, to give the polyhydroxy compound 10, having an amine-terminated linker, isolated as the triethylammonium phosphate salt.

A morpholino oligomer having a 5'-amino group (produced by conversion of the 5'-OH group to a methyl amine) is reacted with disuccinidyl glutarate, giving the activated derivative 12, which then reacts with the amine group of the sugar derivative 10 to give the conjugate 13. Deprotection as usual gives the final product.

The above procedure, which is representative, could be modified, using synthetic methods known in the art, to incorporate other linking groups and saccharides.

Coupling to a transport polypeptide. An antisense oligomer can be attached to a transport polypeptide essentially as described in above-cited WO 97/40854, 1997. The oligomer is preferably attached at or near a terminus of the polypeptide; most preferably, one terminus includes a lipophilic initiator moiety, as described in the above reference, and the other end, the attached oligomer.

Attachment within the peptide chain, to selected amino acid side chains (e.g. lysine, glutamic acid, or cysteine), is also possible. Ester and disulfide linkages are especially preferred if the linkage is to be readily cleaved in the cytosol after delivery of the compound.

In conventional solid-phase peptide synthesis, the peptide is assembled in a C-to-N direction, such that the free end of the peptide is the N-terminus. As described in Example 5, the peptide synthesis can be initiated with a β-alanine, which is effective to shield polar sites at the C-terminus after cleavage, thus facilitating initiation of transport into a cell membrane. Accordingly, the oligomer is typically attached at the N-terminus.

Figure 8A:
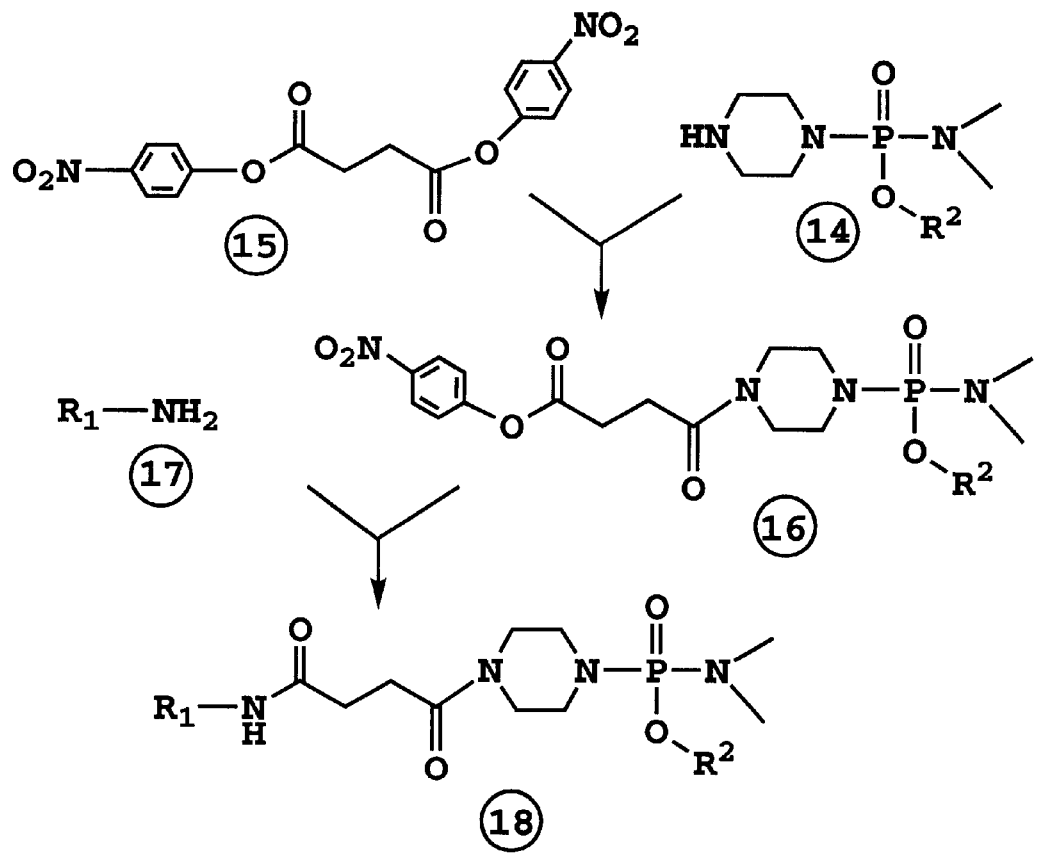
FIGS. 8A and 8B show alternative synthetic methods for conjugating a polypeptide transport moiety to a morpholino-backbone oligomer, to form an antisense conjugate in accordance with the embodiment of the invention illustrated in FIG. 5.
Figure 8B:
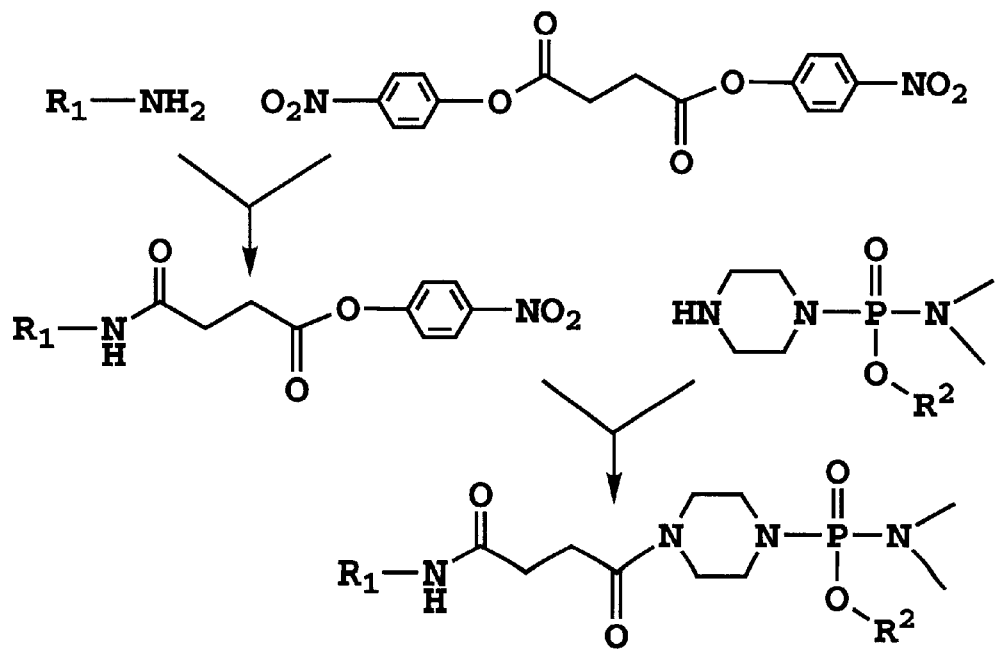

When the oligomer includes a terminal morpholino nitrogen, as in the preferred structures, this attachment can be accomplished by the use of a difunctional linker molecule having activated carboxyl groups, as shown in Examples 11A–B and illustrated in FIGS. 8A–B. A 5'-hydroxyl or amino group on the oligomer may also be utilized.

Alternatively, the antisense oligomer can be attached to the carboxyl terminus of a transport polypeptide. In this case, the carboxyl terminus of the polypeptide (whose side chains are protected if necessary) is activated by means of a reagent such as DCC (dicyclohexylcarbodiimide) and reacted with the terminal morpholino nitrogen, or 5'-hydroxyl or amino group, to form an amide (or ester) linkage. Other coupling agents commonly used to facilitate peptide bond formation may also be used; these include HBTU (2-(1-hydroxy-benzotriazol-1-yl)-1,1,3,3-tetramethyluronium hexafluorophosphate) and BOP (benzotriazol-1-yloxytris(dimethylamino)phosphonium hexafluorophosphate).

For especially large and/or polar compounds, such as the nucleic acid binding oligomers of the invention, transport may be enhanced by attaching multiple, e.g. 2 to 5, polypeptide carriers to a single molecule. This could be accomplished, for example, by the use of a multifunctional linker molecule (such as a polyacid or polyamide), capable of linking multiple peptides, attached to the terminal subunit of the oligomer.

III. Therapeutic Composition

The conjugate of the invention is preferably delivered in a polymer composition that acts to (i) delay flushing of the conjugate from the stomach, particularly when the subject being treated is not in a fed mode, and (ii) release the conjugate into the stomach in a sustained fashion, that is, over a period of up to several hours. The composition may be further designed for adhesion to the lining of the stomach, to prolong residence of the composition in the stomach and to localize conjugate release to the area of infection.

Methods for formulating compositions with the above properties are well known; see, for example, U.S. Pat. Nos. 5,582,837, 5,559,096, 5,007,790, 4,851,232, 4,207,890, 5,273,758, and 4,839,177. Briefly, the composition is formed of a polymer, such as cellulose or an alkyl-substituted cellulose, such as hydroymethycellulose, alginate, guar gum, sucralfate (which has gastric mucoadherent properties), with the desired release, stability and mucoadherent properties. The composition may be formed as a compressed tablet, powder, powder-in-capsule, liquid, or large-particle formulation. A relatively large bolus form of the composition may be advantageous in retaining the composition in the stomach over an extended swelling period.

Methods such as disclosed in the above-cited patents may be followed to produce the composition a desired amount of the conjugate of the invention. The dose required for effective treatment will vary according to the targeted gene and extent of infection. As noted below, a dose of about 5–100 μmoles of drug, e.g., 50–1,000 mg, may be suitable. One advantage of the present invention is that low or no toxicity will be observed even at high conjugate doses. The antisense oligomer is not expected to show toxicity against host genes, since the oligomer sequences are targeted against specific regions of specific bacterial genes. Further the conjugate is unlikely to reach host cells, where the conjugate is not readily absorbed from the gut.

IV. Method of Inhibiting *H. pylori* Infection

In practicing the method of the invention, the conjugate, preferably formulated as a slow-release composition above, is administered orally at a desired dose and dosing schedule. Preferably, the composition is administered several hours before eating, to enhance uptake by the *H. pylori* cells. A total daily dose of between about 5–100 μmoles is preferred, although higher doses may be administered if needed. Such doses would correspond to about 50–1,000 mg of conjugate, assuming a conjugate MW of about 10 kDal. As noted above, overdosing may be indicated, given the lack of side effects.

The dose may be administered once several times daily, once daily, or less often, e.g., for prophylactic purposes. The efficacy of treatment may be followed by established tests, for example, using a tagged urea test (Sanchez, M., et al. (1995) Rev Invest Clin, 47(2):109–116), a $^{13}$C-urea breath test (Yamashiro, Y., et al, (1995) Acta Pediatr Jpn, 37(1):12–16), or a monoclonal antibody saliva test (Husson, M. O., et al.,(1993) Int J Med Microbiol Virol Parasitol Infect Dis, 279(4):466–471). Typically, the conjugate will be administered at least once daily over a period of 15–20 days, until eradication or marked reduction of infection is observed.

The following examples are intended to illustrate, but in no way limit the invention.

Materials. Mercuric cyanide, 2-(aminoethoxy)ethanol, benzyl chloroformate, Dowex®50, 1-(2-mesitylenesulfonyl)-3-nitro-1,2,4-triazolide, and dibenzyl phosphate were obtained from Aldrich Chemicals (Milwaukee, Wis.). AMBERCHROM® 300 SD resin was obtained from TosoHaas. MacroPrep® 50Q ion exchange resin was obtained from BioRad (Richmond, Calif.). Disuccinimidyl glutarate was obtained from Pierce (Rockford, Ill.).

EXAMPLE 1

Synthesis of 5'-OH Morpholino Subunits

The steps in the method are illustrated in FIG. 1E. In the general method, a base-protected ribonucleoside is oxidized with periodate to a 2'-3' dialdehyde (Structure 1). The dialdehyde is closed on ammonia or a primary amine (Structure 2), and the 2' and 3' hydroxyls (numbered as in the parent ribose) are removed by reduction with cyanoborohydride (Structure 3).

An example of this general synthetic scheme is described with reference to the synthesis of a base-protected cytosine ($P_i^*$) morpholino subunit. This procedure yields the base-protected morpholino subunit tritylated on the morpholino nitrogen and having a free 5' hydroxyl (Structure 4).

To 1.6 l of methanol is added, with stirring, 0.1 mole of N-4-benzoylcytidine and 0.105 mole sodium periodate dissolved in 100 ml of water. After 5 minutes, 0.12 mole of ammonium biborate is added, and the mixture is stirred for 1 hour at room temperature, chilled and filtered. To the filtrate is added 0.12 mole sodium cyanoborohydride. After 10 minutes, 0.20 mole of toluenesulfonic acid is added. After another 30 minutes, another 0.20 mole of toluenesulfonic acid is added, and the mixture is chilled and filtered. The solid precipitate is washed with two 500 ml portions of water and dried under vacuum to give the tosylate salt of the free amine, shown in Structure 3.

The base-protected morpholino subunit is then protected at the annular nitrogen of the morpholino ring using trityl chloride (Structure 4), benzhydral nitrophenyl carbonate, or a trialkylsilyl group. For trityl protection, 0.1 mole of the tosylate salt above is added to 2 liters of acetonitrile, with stirring, followed by 0.26 mole of triethylamine and 0.15 mole of trityl chloride. The mixture is covered and stirred for 1 hour at room temperature, after which 100 ml methanol is added, followed by stirring for 15 minutes. After removal of solvent, 400 ml of methanol is added. The solid is thoroughly suspended as a slurry, 5 liters of water is added, and the mixture is stirred for 30 minutes and filtered. The solid is washed with 1 liter of water, filtered, and dried under vacuum. The solid is resuspended in 500 ml of dichloromethane, filtered, and concentrated by evaporation until precipitation just begins, at which point 1 liter of hexane is added, and the mixture is stirred for 15 minutes. The solid is removed by filtering and dried under vacuum.

EXAMPLE 2

Conversion of 5'-Hydroxyl to 5'-Amine

The 5'-hydroxyl of the doubly-protected morpholino subunit prepared in Example 1 (Structure 4, FIG. 1E) is converted to the amine as follows. To 500 ml of DMSO is added 1.0 mole of pyridine, 0.5 mole of trifluoroacetic acid (TFA), and 0.1 mole of the morpholino subunit. The mixture is stirred until dissolved, and then 0.5 mole of diisopropylcarbodiimide (DIC) or dicyclohexylcarbodiimide (DCC) is added. After 2 hours, the reaction mixture is added to 8 liters of rapidly stirred brine, and the mixture is stirred for 30 minutes and filtered. The solid is dried briefly, washed with 1 liter of ice cold hexane, filtered, and added to 0.2 mole of sodium cyanoborohydride in 1 liter of methanol. The mixture is stirred for 10 minutes, 0.4 mole of benzotriazole or p-nitrophenol is added, followed by 0.2 mole of methylamine (40% in $H_2O$) and the preparation is stirred for 4 hours at room temperature. Finally, the reaction mixture is poured into 5 liters of water, stirred to precipitate the product, and the solid (Structure 6, FIG. 1E, where R=methyl) is collected and dried.

EXAMPLE 3

Activation and Coupling of Subunits to Give Phosphoramide Linkages

This example describes the coupling of a 5'-hydroxyl subunit, prepared as in Example 1, to a second subunit having a free morpholino ring nitrogen, to give a phosphordiamidate intersubunit linkage, forming a product as shown in FIG. 1A, where X is the substitution indicated below, and Y is oxygen.

X=N(CH$_3$)$_2$. One mmol of 5'-hydroxyl subunit, base-protected and tritylated on the morpholino nitrogen (e.g. structure 4 of FIG. 1E) is dissolved in 5 ml of dichloromethane. Six mmol of N-ethylmorpholine and 2 mmol of dimethylaminodichlorophosphate (OP(Cl)$_2$N(CH$_3$)$_2$) for Z=O (FIG. 1A), or the thiophosphate analog for Z=S, is added to the solution, followed by the addition of 0.5 mmol of N-methylimidazole. After the reaction is complete as determined by TLC, the solution is washed with aqueous NaH$_2$PO$_4$. The activated subunit is isolated by chromatography on silica gel developed with acetone/chloroform. It is then directly linked to the morpholino nitrogen of a second subunit, by reaction in DMF containing triethylamine sufficient to neutralize the Hcl produced in the reaction, to give the dimer, e.g. as shown in FIG. 1B.

Dimethylaminodichlorophosphate was prepared by refluxing a suspension containing 0.1 mole of dimethylamine hydrochloride in 0.2 mole of phosphorous oxychloride for 12 hours and distilling (bp 36° C. at 0.5 mm Hg). Dimethylaminodichlorothiophosphate was prepared by refluxing a suspension containing 0.1 mole of dimethylamine hydrochloride in 0.2 mole of thiophosphoryl chloride for 18 hours and distilling (bp 85° C. at 15 mm Hg).

X=—O—$CH_2CH_3$. One mmol of 5'-hydroxyl subunit, base-protected and tritylated on the morpholino nitrogen (Structure 4 of FIG. 1E), is suspended in 80 ml of benzene, and 2.2 mmol of N-methylimidazole is added. After the subunit is dissolved, 1.2 mmol of ethyl dichlorophosphate for Z=O (FIG. 1A) or ethyldichlorothiophosphate for Z=S, is added. After 1 hour, the reaction solution is washed with aqueous $NaH_2PO_4$. The activated subunit is isolated by chromatography on silica gel developed with ethyl acetate. It is then directly linked to the morpholino nitrogen of a second subunit, by reaction in DMF containing triethylamine sufficient to neutralize the HCl produced in the reaction, to give the dimer, e.g. as shown in FIG. 1C.

Note: When ethyldichlorothiophosphate (Z=S) is used for activation of the subunits, improved yields are obtained with the following modifications. One mmol of 5'-hydroxyl subunit, base-protected and tritylated on the morpholino nitrogen (Structure 4 of FIG. 1E), is suspended in 20 ml of chloroform. To this solution 1 ml of N-methylimidazole is added, followed by 1.6 ml of ethyldichlorothiophosphate (Aldrich Chem. Co.). After 1 hour the subunit product is purified by silica gel chromatography developed with 20% acetone/80% chloroform. This activated subunit is coupled to the morpholino nitrogen of a second subunit as described above.

X=—$CH_3$. One mmol of 5'hydroxyl subunit, base-protected and tritylated on the morpholino nitrogen (Structure 4 of FIG. 1E), is dissolved in 20 ml of dichloromethane. To this solution 4 mmol of N-ethylmorpholine and 1.1 mmol of methylphosphonic dichloride, for Z=O (FIG. 1A) or methylthiophosphonic dichloride, for Z=S, is added, followed by 1 mmol of N-methylimidazole. After one hour the reaction solution is washed with aqueous $NaH_2PO_4$. The activated subunit is isolated by chromatography on silica gel developed with ethyl acetate. It is then directly linked to the morpholino nitrogen of a second subunit, by reaction in DMF containing triethylamine sufficient to neutralize the HCl produced in the reaction, to give the dimer.

The alkylphosphonoamidate intersubunit linkage is very stable to ammonia used for base deprotection. In contrast, the linkage is sensitive to strong acids. For instance, the linkage has a half time of cleavage of about 3 hours in 2% dichloroacetic acid in dichloromethane. However, the linkage showed no detectable cleavage after 18 hours in 2% acetic acid in trifluoroethanol, conditions suitable for detritylation of the morpholino nitrogen.

X=—F. One mmol of 5'-hydroxyl subunit, base-protected with groups removable by a beta elimination mechanism and tritylated on the morpholino nitrogen, is dissolved in 20 ml of dichloromethane, to which is added 6 mmol of N-methylimidazole, followed by 2.5 mmol of fluorophosphoric acid. DCC (5 mmol) is added, and the solution is stirred for 3 hours. The solution is then washed with aqueous $NaH_2PO_4$, and the organic phase is dried under reduced pressure to give the fluorophosphate salt. The product is purified by silica gel chromatography developed with a methanol/chloroform mixture 1% in pyridine to give the pyridinium salt. After drying, the purified product is suitable for coupling to a 5'-protected subunit having a free morpholino nitrogen, using DCC in dichloromethane, to yield the dimer.

Oligomers containing the fluorophosphoramidate intersubunit linkage should not be exposed to strong nucleophiles, such as ammonia. Consequently, bases of the subunits used for assembling such polymers should be protected with groups which can be cleaved without the use of strong nucleophiles. Protective groups cleavable via a beta elimination mechanism, as described, for example, in U.S. Pat. No. 5,185,444, are suitable for this purpose.

EXAMPLE 4

Activation and Coupling of Subunits to give a Sulfonamide Linkage

This example describes the coupling of a 5'-methylamino subunit, prepared as in Example 2, to a second subunit having a free morpholino ring nitrogen, to give a sulfonamide intersubunit linkage, forming a structure as shown in FIG. 1D, where R is methyl.

The 5'-methylamino subunit is dissolved in pyridine and treated with 1.1 equivalents of sulfur tioxide/pyridine complex. After one hour at room temperature, water is added, the solution stirred at room temperature for 30 minutes, and the solution is evaporated and the residue chromatographed on silica using 5–20% methanol:chloroform containing 1% pyridine. The crude product, the pyridinium salt of the sulfamic acid, is activated immediately by first dissolving in pyridine and evaporating, then repeating the evaporation from pyridine. The residue is dissolved in dichloromethane at room temperature and cooled to $-78°$ C. Pyridine (5 equivalents) is added followed by a 1.9 M solution of phosgene in toluene (2.5 equivalents). The reaction is warmed to 25° C. After stirring for 10 minutes, the reaction is recooled to −78° C. and treated with 10 equivalents of methanol. The solution is evaporated under high vacuum and the residue chromatographed on silica using ethyl aceteate/chloroform eluent.

The activated subunit is then reacted with a second subunit, having an unprotected morpholino ring nitrogen, to give the dimer.

EXAMPLE 5

Preparation of a Polypeptide ("Molecular Engine") Composition

Assembly. A peptide synthesis resin is prepared so that β-alanine will comprise the C-terminal residue of the polypeptide, as illustrated in FIG. 3C, thus increasing the lipophilicity of this terminus. One gram of 1% crosslinked polystyrene resin containing 0.7 mmol p-alkoxybenzyl alcohol (Sigma Chem. Co., St. Louis, Mo.) is dissolved in 8 ml of N-methylpyrrolidinone (NMP), and 0.62 g of fluorenylmethoxycarbonyl (FMOC) β-alanine is added, followed by 316 μl of N,N'-diisopropyl carbodiimide and 41 μl N-methylimidazole. This slurry is incubated with agitation at 37° C. for 100 minutes, then washed thoroughly with NMP, followed by $CH_2Cl_2$, drained, and dried. This affords a resin with a loading of about 250 μmol β-alanine-FMOC per gram of material. Subsequent addition of protected/activated amino acids to extend the polypeptide is then carried out, e.g. according to the method of Atherton et al. (1988), which employs N-fluorenylmethoxycarbonylpentafluorophenyl amino acid esters.

End Capping. In cases where the compound to be transported is not linked through the N-terminal amine, it is generally desirable to shield or delete at least some of the N-terminal polar sites. This can be achieved, for example, by cleaving the FMOC moiety from the N-terminus of the completed resin-bound polypeptide and then reacting the N-terminus with glutaric anhydride or acetic anhydride. This serves to cap the am ino group and, in the case of the dianhydride, shields additional polar sites by hydrogen bonding, as shown in FIGS. 4B–4C.

Side Chain Attachment Sites. When it is desired to attach the compound to be transported at one or more positions other than the terminus of the polypeptide, a suitably-protected lysine or cysteine can be incorporated at the selected attachment position(s). Following cleavage of the completed polypeptide from the synthesis resin and sidechain deprotection, the compound can be attached to the resulting amine or sulfhydryl moiety.

EXAMPLE 6

Formation of the Benzyl Carbamate of 2-(aminoethoxy)ethanol 2-(Aminoethoxy)ethanol (3 mmol) was treated with benzyl chloroformate (1 mmol) in dichloromethane with vigorous stirring at 0° C. After 30 minutes, the solution was warmed to room temperature and stirred an additional hour. The solution was twice washed with pH=7 ph osphate buffer, then with brine, then dried over sodium sulfate and evaporated to dryness. The benzyl carbamate was purified by chromatography on silica using 0–10% methanol in chloroform.

EXAMPLE 7

Formation of Alpha-D-Mannapyranose, 1,2,3,4-Tetraacetate, 6-Dibenzylphosphate (8) by Phosphorylation of Alpha-D-Mannopyranose, 1,2,3,4-Tetraacetate (7)

Alpha-D-mannopyranose, 1,2,3,4-tetraacetate, 7 (FIG. 6) (see Reynolds and Evans, *J. Amer. Chem. Soc.* 62:66–69 (1940)) (1 mmol) and dibenzyl phosphate (1 mmol) were dissolved in anhydrous pyridine and the mixture was concentrated. This was repeated two more times. The residue was dissolved in dry pyridine and treated with 1-(2-mesitylenesulfonyl)-3-nitro-1,2,4-triazolide (1.5 mmol). After stirring for 24 hours at room temperature, the reaction was quenched by the addition of water, the pyridine evaporated, and the residue dissolved in ethyl acetate. The organic layer was washed sequentially with 0.2 M HCl, 0.2 M sodium bicarbonate, water, and brine. The organic layer was dried over sodium sulfate, evaporated under vacuum, and the pure product 8 obtained by chromatography on silica, eluting with ethyl acetate/hexane mixtures.

EXAMPLE 8

Formation of 2-(Benzyloxycarbonylaminoethoxy) ethyl Alpha-D-Mannopyranoside-1,3,4-Triacetate-6-Dibenzyl Phosphate (9)

To a stirred and cooled (ice bath) solution of alpha-D-mannopyranose-1,2,3,4-tetraacetate-6-dibenzylphosphate 8 (2 mmol) in acetic anhydride (4 mL) and phosphorus tribromide (1.4 mL) was added water (1.7 mL) dropwise during 30 minutes. The mixture was stirred until TLC (chloroform-acetone) indicated completion of reaction. The mixture was diluted with cold chloroform, washed with cold water, cold 10% aqueous bicarbonate, and cold water again, dried over magnesium sulfate, and evaporated to yield the crude bromide. The bromide was dissolved in acetonitrile and added dropwise to a stirred solution of the benzyl carbamate of 2-(aminoethoxy)ethanol (1 mmol) and mercuric cyanide in acetonitrile-nitromethane (20:1) at 20° C. The mixture was stirred for 3 hours at this temperature, diluted with chloroform, washed with 1 M potassium bromide solution, then water, dried over magnesium sulfate and concentrated to dryness. The residue was chromatographed on silica gel by eluting with ethyl acetate/hexane mixtures.

EXAMPLE 9

Formation of 2-(Aminoethoxy)ethyl Alpha-D-Mannopyranoside-6-Dihydrogen Phosphate (10)

2-(Benzyloxycarbonylaminoethoxy)ethyl alpha-D-mannopyronoside-1,3,4-triacetate-6-dibenzyl phosphate 9 (1 mmol) was dissolved in methanol/THF (2:1) and treated with 2 M sodium methoxide in methanol (4 mmol). The solution was neutralized with Dowex® 50 sulfonic acid ion exchange resin (H+), filtered, and evaporated. The residue (1 mmol) was dissolved in aqueous ethanol containing 10% Pd/C (0.1 g per gram substrate) and triethylamine (3 mmol). The mixture was shaken at 45 psi and room temperature until all benzyl groups had been cleaved. The solution was filtered and evaporated to provide the triethylammonium salt of the product 10.

EXAMPLE 10

Formation of a Mannose Conjugated Morpholino Oligomer

A morpholino oligomer 11 (FIG. 7) possessing a 5'-terminal methylamino group was produced by the method described in U.S. Pat. No. 5,185,444 (Summerton and Weller, 1993). While still on the resin, the terminal trityl group was removed under the usual conditions and the 3'-terminus substituted with a monomethoxytrityl group. This was done by treating the resin-bound detritylated oligomer with a solution of dimethyoxytrityl chloride (0.5 M) in dichloromethane-tetramethylenesulfone (4:1) containing N-ethyl morpholine for 30 minutes at room temperature. After thorough washing, the oligomer was removed from the resin, as described in U.S. Pat. No. 5,185,444 (1993). It is advantageous to allow the 20% DBU/DMF solution containing the freed oligomer to drop into ether containing 2-ethylhexanoic acid. The precipitate is collected by centrifugation and washed thoroughly with ether, then dried in a slow stream of dry nitrogen until chalky, then under high vacuum.

The dried, precipitated oligomer was dissolved in NMP, N-ethylmorpholine was added, and the solution treated with disuccinimidyl glutarate (0.2 M). After 4 hours at room temperature, the reaction mixture was added dropwise to excess ether to precipitate the product 12. If desired, the product may be redissolved in NMP and reprecipitated. The precipitate was washed well with ether, dissolved in NMP containing triethylamine, and treated with a DMSO solution of 2-(aminoethoxy)ethyl alpha-D-mannopyranoside, 6-dihydrogen phosphate triethylammonium salt 10. After 2 hours at room temperature, the solution was diluted with 4 volumes of conc. ammonia and treated at 45° C. for 16 hours. The ammonia was evaporated under high vacuum and the crude ammonolysis product purified on a column of MacroPrep 50Q ion exchange resin, using a gradient of 0–1 M sodium hydroxide solution to adjust the pH to 8.0. The mixture was applied to the top of an AMBERCHROM 300

SD resin and the product eluted using a gradient of 0–80% acetonitrile in water. The pooled product containing fractions when then lyophilized to yield the oligomer 13 having a phosphomannosyl group (sodium salt) on the 5'-terminus.

EXAMPLE 11

Preparation of a Polypeptide—Morpholino Antisense Oligomer Conjugate

Structures and subunit sequences of the Morpholino oligomer and polypeptide employed in this Example are as follows, with reference to FIGS. 8A–8B:

$R_1$ = —
ELLDLELLDLELLDLELLDLELLDLELL-DLELLDLELLDLELLβ where D=aspartic acid, E=glutamic acid, L=leucine, β=β-alanine $R_2$=5'-G*G*UG*G*UUC*C*UUC*UC*A*G*UC*G*G*-acetyl where
A*=Morpholino 6-benzoyladenine
C*=Morpholino 6-benzoylcytosine
G*=Morpholino 6-phenylacetylguanine
U=Morpholino uracil Procedure 1 (FIG. 8A): Base-protected Morpholino antisense oligomer 14 (17 mg, 2 μMol) is suspended in 200 μl NMP. Bis(p-nitrophenyl) succinate 15 (7.2 mg, 20 μmol) is added, and the preparation is incubated for 4 hours at 43° C. The unreacted succinate is removed by precipitating the Morpholino-succinate product from 30 ml of acetonitrile, centrifuging, discarding the supernatant, resuspending the pellet in 0.4 ml of NMP, adding to 30 ml of acetonitrile, centrifuging, discarding the supernatant, and drying the pelleted Morpholino-succinate product 16 under high vacuum.

The Morpholino antisense oligomer with succinate linker 16 (2 μmol) is then added to 31 mg (6 μmol) of the deprotected 44-amino acid polypeptide $R_1$—$NH_2$, shown at 17, having a free amine moiety on the N-terminus. DMF (150 μl) is added and the mixture stirred in a warm water bath until dissolution is complete. The reaction mixture is then incubated at 43° C. for 72 hours and diluted with 200 μL NMP. Conc. $NH_4OH$ (600 μL) is added, and the solution is incubated 18 hours at 43° C. to deprotect the purine and pyrimidine bases of the Morpholino antisense oligomer. The product 18 is purified by ion exchange chromatography followed by reverse phase HPLC.

Procedure 2 (FIG. 8B): In this procedure, the activated succinate linker is added to the polypeptide, and the adduct is reacted with the Morpholino antisense oligomer. Accordingly, an NMP suspension of 180 mg of resin/polypeptide, prepared by standard solid phase peptide synthesis (Example 5), is treated with 20% piperidine in NMP, then washed repeatedly with NMP. Bis(p-nitrophenyl) succinate (150 mg) is dissolved in 0.9 ml NMP, added to a short fritted column containing the resin/polypeptide preparation and incubated 2 hours at 43° C. Excess succinate linker is washed out, and the product is cleaved from the synthesis resin to give a polypeptide-succinate product. This product (32 mg; 6 μmol) is combined with 17 mg (2 μmol) Morpholino antisense oligomer 14, containing a 5' secondary amine moiety, in 150 μl DMF. The mixture is stirred in a warm water bath until dissolution is complete. The reaction mixture is then incubated at 43° C. for 48 hours. Thereafter, the reaction mixture is diluted with 200 μl NMP, 600 μl of conc. $NH_4OH$ is added, and the solution is incubated 18 hours at 43° C. to deprotect the purine and pyrimidine bases of the Morpholino antisense oligomer. The product 18 is purified as described above.

In this Example, the N-terminus of the polypeptide is used for attachment of the Morpholino oligomer. Alternatively, the C-terminus may be used for attachment. In this case, the N-terminus may be capped and/or shielded as described above, and the carboxyl terminus is reacted with a suitable activating reagent, e.g. dicyclohexylcarbodiimide, and an amide linkage formed between this terminus and the terminal morpholino nitrogen of the Morpholino antisense oligomer.

Although the invention has been described with respect to preferred conjugates, compositions, and methods, it will be appreciated that various changes and modifications may be made, within the scope of the claim, without departing the invention.

It is claimed:

1. A method of treating *H. pylori* infection in a subject, comprising administering to the subject, by oral route, a therapeutically effective amount of an antisense conjugate composed of
    (a) a nuclease-resistant antisense oligomer effective to inhibit *H. pylori* infection in the subject by base-specific Watson-Crick binding to an *H pylori* mRNA transcript, and
    (b) conjugated to the antisense moiety, a transport moiety effective to facilitate uptake of the composition from the environment of the stomach into the cytoplasm of *H. pylori* cells by active transport or by pH-gradient transport across the cell membrane of *H. pylori*.

2. The method of claim 1, wherein the antisense oligomer has an uncharged morpholino backbone.

3. The method of claim 1 or 2, wherein the antisense oligomer has a sequence that spans the AUG start codon of an *H. pylori* gene selected from the group consisting of the vacA, cagA, cai, a porin, nixA, pfr, neutrophil activating factor, urease, metal-binding polypeptide, and copper-binding protein genes.

4. The method of claim 3, wherein the oligomer has a sequence selected from the group consisting of SEQ ID NOS: 1–11.

5. The method of claim 4, wherein the sequence is selected from the group consisting of SEQ ID NOS:1, 5, and 6.

6. The method of claim 1, wherein the transport moiety is D-galactose or L-arabinose, and uptake of the conjugate is by active transport.

7. The method of claim 1, wherein the transport moiety is a polypeptide containing one or more pairs of carboxyl groups, where
(i) the carboxyl groups of a pair are separated by zero, two or three amino acids, (ii) the polypeptide has a length of between about 8 and about 100 amino acid residues, and (iii) the polypeptide is effective to undergo a reversible transition between a lipophilic form at the pH of the stomach, and a hydrophilic form at the pH of the cytoplasm of *H. pylori* cells, and uptake of the conjugate is by pH-gradient transport.

8. The method of claim 7, wherein the transport moiety further includes an initiator moiety at one end region of the polypeptide, to facilitate entry of said end region into the membrane of *H. pylori* cells.

9. An antisense conjugate for treating *H. pylori* infection comprising
    (a) a nuclease-resistant antisense oligomer effective to inhibit *H. pylori* infection in the subject by base-specific Watson-Crick binding to an *H pylori* mRNA transcript, wherein the antisense oligomer has a sequence that spans the AUG start codon of an *H. pylori* gene selected from the group consisting of the vacA, cagA, cai, nixA, pfr, neutrophil activating factor, urease, His-rich metal-binding polypeptide, and copper-binding protein genes, and (b) conjugated to the antisense moiety, a transport moiety effective to facilitate uptake of the composition from the environment of the stomach into the cytoplasm of *H. pylori* cells by active transport or by pH-gradient transport across of the cell membrane of *H. pylori*, wherein the transport moiety is selected from the group consisting of (i) D-galactose, (ii) L-arabinose, and (iii) a polypeptide containing one or more pairs of carboxyl groups, where
  (a) the carboxyl groups of a pair are separated by zero, two or three amino acids,
  (b) the polypeptide has a length of between about 8 and about 100 amino acid residues, and
  (c) the polypeptide is effective to undergo a reversible transition between a lipophilic form at the pH of the stomach, and a hydrophilic form at the pH of the cytoplasm of *H. pylori* cells.

10. The conjugate of claim 9, wherein the antisense oligomer has an uncharged morpholino backbone.

11. The conjugate of claim 9 or 10, wherein the oligomer has the sequence selected from the group consisting of SEQ ID NOS:1–11.

12. The conjugate of claim 11, wherein the oligomer has a sequence selected from the group consisting of SEQ ID NOS: 1, 5, and 6.

13. The conjugate of claim 9, wherein the transport moiety further includes an initiator moiety at one end region of the polypeptide, to facilitate entry of said end region into the membrane of *H. pylori* cells.

14. A composition for use in treating *H. pylori* infection in a subject, comprising, (i) a swellable polymer matrix designed for sustained swelling in the stomach, and (ii) carried in the matrix, for release from the matrix as the matrix swells, an antisense conjugate for treating *H. pylori* composed of (a) a nuclease-resistant antisense oligomer effective to inhibit *H. pylori* infection in the subject by base-specific Watson-Crick binding to an *H pylori* mRNA transcript, wherein the antisense oligomer has a sequence that spans the AUG start codon of an *H. pylori* gene selected from the group consisting of the vacA, cagA, cai, nixA, pfr, neutrophil activating factor, urease, His-rich metal-binding polypeptide, and copper-binding protein genes, and (b) conjugated to the antisense moiety, a transport moiety effective to facilitate uptake of the composition from the environment of the stomach into the cytoplasm of *H. pylori* cells by active transport or by pH-gradient transport across of the cell membrane of *H. pylori*, wherein the transport moiety is selected from the group consisting of (i) D-galactose, (ii) L-arabinose, and (iii) a polypeptide containing one or more pairs of carboxyl groups, where
  (a) the carboxyl groups of a pair are separated by zero, two or three amino acids,
  (b) the polypeptide has a length of between about 8 and about 100 amino acid residues, and
  (c) the polypeptide is effective to undergo a reversible transition between a lipophilic form at the pH of the stomach, and a hydrophilic form at the pH of the cytoplasm of *H. pylori* cells.

15. The composition of claim 14, wherein the polymer matrix is selected from the group consisting of alginate, other natural gums, sucralfate, and a cellulose.

* * * * *